United States Patent
Richter

(10) Patent No.: US 10,712,148 B2
(45) Date of Patent: Jul. 14, 2020

(54) OPTICAL DETERMINATION OF THE POSITION OF THE STOPPER IN GLASS AMPOULES

(71) Applicant: SANOFI-AVENTIS DEUTSCHLAND GMBH, Frankfurt am Main (DE)

(72) Inventor: Rene Richter, Tharandt (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 15/247,493

(22) Filed: Aug. 25, 2016

(65) Prior Publication Data

US 2016/0363438 A1    Dec. 15, 2016

Related U.S. Application Data

(63) Continuation of application No. 12/415,241, filed on Mar. 31, 2009, now Pat. No. 9,435,666, which is a (Continued)

(30) Foreign Application Priority Data

Oct. 7, 2006    (DE) .................. 10 2006 047 537

(51) Int. Cl.
*G01D 5/34*        (2006.01)
*G01B 11/02*       (2006.01)
(Continued)

(52) U.S. Cl.
CPC .......... *G01B 11/14* (2013.01); *A61M 5/1684* (2013.01); *A61M 5/24* (2013.01);
(Continued)

(58) Field of Classification Search
CPC ...... A61M 5/31525; A61M 2205/6063; A61M 2205/3306; A61M 2205/3379;
(Continued)

(56) References Cited

U.S. PATENT DOCUMENTS

| | | | |
|---|---|---|---|
| 1,737,126 A | * | 11/1929 | Reyling ............... G01F 23/292 340/619 |
| 4,498,843 A | | 2/1985 | Schneider et al. |

(Continued)

FOREIGN PATENT DOCUMENTS

| | | |
|---|---|---|
| DE | 820971 C | 11/1951 |
| DE | 4211003 A1 | 10/1992 |

(Continued)

OTHER PUBLICATIONS

Definitions of "silhouette" and "photosensitive". Retrieved from Dictionary.com [Online] on Nov. 13, 2017.*

(Continued)

*Primary Examiner* — Jenna Zhang
(74) *Attorney, Agent, or Firm* — McCarter & English, LLP

(57) ABSTRACT

A method for determining a position of a component in a medical apparatus along a travel distance. The method comprising the steps of generating light by a light source; fixing the component movably along a travel distance; providing a photosensitive sensor surface, and generating a silhouette of the component on the sensor surface by irradiating the component with light from the light source. Data relating to the silhouette is converted by a data processing unit into the position of the component along the travel distance. The component whose position is determined may comprise a stopper of a cartridge.

22 Claims, 2 Drawing Sheets

Related U.S. Application Data continuation of application No. PCT/EP2007/008363, filed on Sep. 26, 2007.

(51) Int. Cl.
| | |
|---|---|
| *G01F 11/02* | (2006.01) |
| *A61M 5/315* | (2006.01) |
| *G01B 11/14* | (2006.01) |
| *A61M 5/168* | (2006.01) |
| *A61M 5/24* | (2006.01) |
| *G01F 23/292* | (2006.01) |
| *A61M 5/145* | (2006.01) |

(52) U.S. Cl.
CPC ....... *A61M 5/31525* (2013.01); *G01B 11/024* (2013.01); *G01D 5/342* (2013.01); *G01F 11/029* (2013.01); *A61M 5/1452* (2013.01); *A61M 2205/3306* (2013.01); *A61M 2205/3379* (2013.01); *A61M 2205/3389* (2013.01); *A61M 2205/6063* (2013.01); *G01F 23/292* (2013.01); *G01F 23/2927* (2013.01); *Y02A 90/26* (2018.01); *Y10T 29/49826* (2015.01)

(58) Field of Classification Search
CPC .... A61M 2205/3389; A61M 2205/583; A61M 5/24–5/5288; G01N 2201/0633; G01D 5/342; G01F 11/029; G01F 11/024; G01F 23/292; G01F 23/2925; G01F 3/16; G01F 11/027; G01F 11/00; F15B 15/28; F15B 15/2869–2876

See application file for complete search history.

(56) References Cited

U.S. PATENT DOCUMENTS

| | | | | |
|---|---|---|---|---|
| 4,566,337 | A * | 1/1986 | Smart | G01F 1/28 73/861.56 |
| 4,699,186 | A * | 10/1987 | Palin | A61M 5/1782 141/2 |
| 4,956,560 | A * | 9/1990 | Smith, Jr. | B67C 3/20 250/223 B |
| 5,073,720 | A | 12/1991 | Brown | |
| 5,310,658 | A * | 5/1994 | Berndt | C12Q 1/04 422/79 |
| 5,379,651 | A * | 1/1995 | Doolittle | G01F 1/22 73/861.56 |
| 5,463,228 | A * | 10/1995 | Krause | G01F 23/292 250/577 |
| 5,523,560 | A * | 6/1996 | Manique | G01N 21/9027 250/223 B |
| 5,662,612 | A | 9/1997 | Niehoff | |
| 5,747,824 | A | 5/1998 | Jung et al. | |
| 6,013,020 | A * | 1/2000 | Meloul | A61N 5/1002 600/7 |
| 6,113,578 | A * | 9/2000 | Brown | A61B 5/14532 604/207 |
| 6,385,507 | B1 * | 5/2002 | Buijtels | G01N 21/95684 219/267 |
| 6,585,698 | B1 * | 7/2003 | Packman | A61M 5/24 604/207 |
| 6,937,339 | B2 * | 8/2005 | Yamazaki | G01N 21/9027 356/239.6 |
| 7,033,338 | B2 | 4/2006 | Vilks et al. | |
| 7,033,389 | B2 | 4/2006 | Sherry | |
| 8,036,444 | B2 * | 10/2011 | Nielsen | G01N 21/9027 250/223 B |
| 9,435,666 | B2 | 9/2016 | Richter | |
| 2001/0056258 | A1 * | 12/2001 | Evans | A61M 5/31533 604/131 |
| 2002/0102055 | A1 * | 8/2002 | Zweiback | G02B 6/02138 385/37 |
| 2003/0105430 | A1 * | 6/2003 | Lavi | A61M 5/2033 604/136 |
| 2004/0135078 | A1 * | 7/2004 | Mandro | G01D 5/34776 250/231.13 |
| 2006/0154327 | A1 * | 7/2006 | Bachur, Jr. | C12M 41/34 435/34 |
| 2006/0178578 | A1 * | 8/2006 | Tribble | B65B 3/003 600/432 |
| 2008/0230720 | A1 * | 9/2008 | Nielsen | G01N 21/9027 250/492.1 |

FOREIGN PATENT DOCUMENTS

| | | |
|---|---|---|
| DE | 19643813 A1 | 4/1998 |
| DE | 29908111 U1 | 7/1999 |
| DE | 10236669 A1 | 2/2004 |
| EP | 0151854 B1 | 8/1985 |
| EP | 0858349 B1 | 8/1998 |
| EP | 1535737 A1 | 6/2005 |
| EP | 1563859 A1 | 8/2005 |
| JP | S58-165015 A | 9/1983 |
| JP | 5-31881 A | 2/1993 |
| JP | 2005-021431 A | 1/2005 |
| JP | 2006-224990 A | 8/2006 |
| WO | 1995/21369 A1 | 8/1995 |
| WO | 2001/56635 A1 | 8/2001 |
| WO | 2004/009163 A1 | 1/2004 |
| WO | 2006/064976 A2 | 6/2006 |
| WO | 2006/120182 A1 | 11/2006 |

OTHER PUBLICATIONS

ISO—International Organization for Standarization, Pen-injectors for medical use, Part 1: Pen-injectors—Requirements and test methds. ISO 11608-1, First Edition, 32 pages, Dec. 15, 2000.
ISO—International Organization for Standarization, Pen-injectors for medical use, Part 2: Needles—Requirements and test methods. ISO 11608-2, First Edition, 18 pages, Dec. 15, 2000.
ISO—International Organization for Standarization, Pen-injectors for medical use, Part 3: Finished cartridges—Requirements and test methods. ISO 11608-3, First Edition, 22 pages, Dec. 15, 2000.
International Search Report and Written Opinion for Application No. PCT/EP2007/008363, dated Jan. 15, 2008. 14 pages.
International Preliminary Report on Patentability for Application No. PCT/EP2007/008363, dated Jun. 23, 2009. 13 pages.

* cited by examiner

//+  # OPTICAL DETERMINATION OF THE POSITION OF THE STOPPER IN GLASS AMPOULES

CROSS-REFERENCE TO RELATED APPLICATIONS

This application is a continuation of U.S. patent application Ser. No. 12/415,241 filed on Mar. 31, 2009, which is a continuation of PCT/EP2007/008363 filed on Sep. 26, 2007, which claims priority to German Application No. 102006047537.2 filed on Oct. 7, 2006, the entire contents of each of which are hereby incorporated by reference.

The invention relates to a method for determining the stopper position of a medicament cartridge in a medical apparatus by means of a light source and photosensitive sensor surface.

Many pharmaceuticals must be injected into the body. This applies in particular to those which are inactive or are crucially low of activity on oral administration. These pharmaceuticals include in particular proteins (such as, for example, insulin, growth hormones, interferons), carbohydrates (e.g. heparin), antibodies or most vaccines. Syringes, medicament pens or medicament pumps are predominantly used for injection into the body.

The conventional insulin injection apparatus is the insulin syringe. This has been used since the start of insulin therapy, but has in recent years been displaced stepwise by introduction of the insulin pen, especially in Germany. Nevertheless, syringes are at present irreplaceable, e.g. if an insulin pen is lost or defective, and are used by many diabetics in combination with insulin pens. The freedom from maintenance and the universal availability is advantageous, especially during journeys.

Insulin syringes differ in their designation and graduation according to the concentration of the insulin to be used, U40 or U100. The insulin can be taken either from vials or else from the prefilled cartridges for insulin pens. This makes it possible to mix different types of insulin and reduces the number of injections necessary. Particular care about freedom from bubbles is necessary when the insulin is drawn into the syringe. The directly visible insulin dose which has been drawn in makes it possible for the user easily to check the amount of insulin injected. Nevertheless, skill and regular use are necessary for error-free administration with insulin syringes.

A further injection apparatus which is now very widely used around the world and especially in Europe is the insulin pen.

This medical apparatus which is the size of a marker pen was developed in the mid 1980s and is employed mainly for more intensive insulin therapy. A substantial innovation compared with insulin syringes is their use of an exchangeable medicament container. This container, also called carpule or cartridge, is filled with insulin when supplied by the manufacturer and is inserted into the insulin pen before use. When the pen is operated, a needle pierces the sealing disk of the cartridge and achieves parenteral injection of the preselected dose on administration of the insulin. An injection and release mechanism generates during the injection an injection stroke which advances a plunger or stopper in the cartridge and causes the preselected dose to be delivered into the target tissue. The mechanism usually consists of a rigid plunger stem with an overall length corresponding to the cartridge stopper stroke.

Insulin pens are divided into disposable and reusable ones. In the case of disposable ones, the cartridge and the metering mechanism form a unit prefabricated by the manufacturer and are disposed of together after the cartridge is emptied. Reuse of the metering mechanism is not intended. In contrast to prefabricated pens, reusable pens make increased demands on the user. Thus, when the cartridge is changed, the plunger stem must be retracted into the starting position. This takes place, depending on the model, by twisting or sliding the plunger stem while simultaneously actuating a special function in the metering mechanism. This must be carried out very carefully by the user because malfunctions, e.g. sticking of the plunger stem, may occur occasionally owing to the daily use and the high mechanical stress.

Reusable insulin pens are further divided into manual and semiautomatic pens. In the case of manual pens, the user exerts a force with the finger to actuate the injection button and thus determines the duration and progress of the injection. By contrast, with semiautomatic insulin pens, use is preceded by a manual tensioning of a spring which stores the necessary energy for injection. In the actual injection step, the spring is released by the user. The speed of injection is fixed by the power of the spring and cannot be adapted to personal needs.

WO 2004 009 163 discloses an optical sensor for use in a medicament administration system by means of which the displacement of the plunger stem is possible on the basis of transparent or reflecting markings. The light source used is an array of LEDs, whereas linear or two-dimensional CCD elements are employed as imaging elements.

EP 858349 B1 discloses a device for optical measurement and electronic recording of a dose with a light source and an optical detector. The detector is disposed so that it detects the total amount of light reflected by a syringe, and the reflected amount of light is related to the amount of liquid in the syringe.

WO 2001 566 35 discloses an apparatus for administering a medicament comprising a sensor element with which a recognition element and/or the state of operation of a container (e.g. the distance a plunger has been pushed in) can be recognized.

Figure 1:
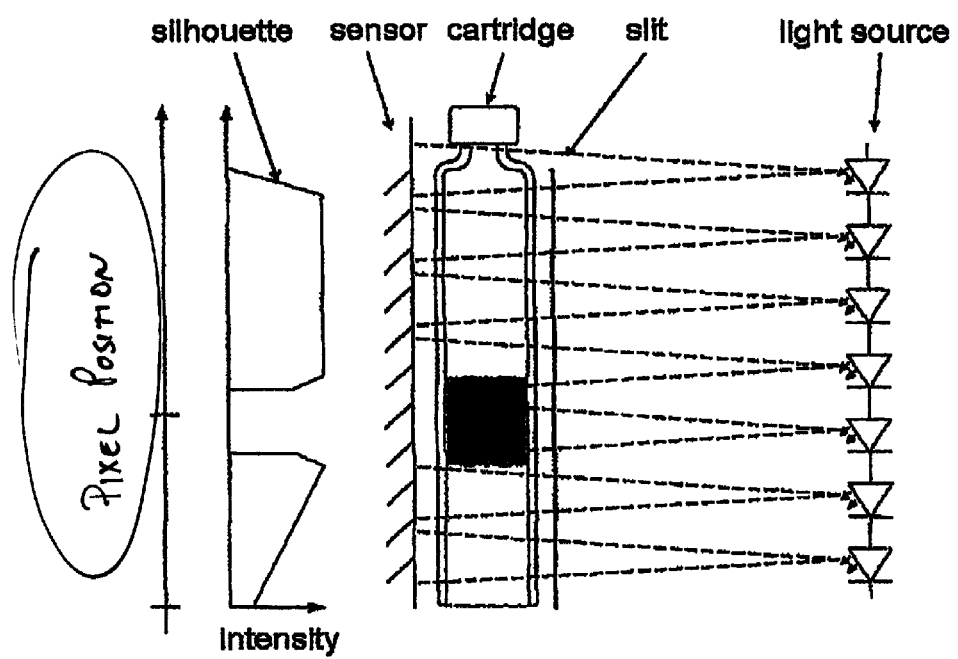
FIG. 1 shows a sensor system to identify the stopper position (without evaluation electronics).

The invention relates to a method for determining the position of a component in a medical apparatus along a travel distance by means of a) a light source and b) a holder which movably fixes the component along a travel distance, and c) a photosensitive sensor surface, wherein firstly a silhouette of the component is generated on the sensor surface by irradiation of the component with light from a), then the data relating to the silhouette on the sensor surface are converted by a data-processing unit into the position of the component relative to the travel distance.

A data processing unit consists firstly of hardware components such as in particular a central arithmetic unit, one or more memories, output and control devices, and the technical connections between these parts, and secondly of software components such as, in particular, an operating system, and a program for controlling and evaluating the carrying out of a position determination.

The method relates in one embodiment to the determination of the position of the stopper of a cartridge for a pharmaceutical and in particular to the determination of the position of the stopper of an insulin cartridge. The movement of the stopper of a cartridge for a pharmaceutical such as, for example, insulin within a medical apparatus (e.g. insulin pen, insulin pump) corresponds to the delivered amount of pharmaceutical. Determination of the position of stopper in a cartridge when a medical apparatus is operated therefore serves to control and monitor the delivered amount of pharmaceutical (e.g. insulin).

The method relates in a further embodiment to determination of the position of a component which is part of the adjusting device by means of which the amount of pharmaceutical to be delivered is preset. This component, which is part of the adjusting device, may consist of a geometrically shaped (round, oval, square, rectangular, stellate, combined shape and others) projection which is fixedly connected to the adjusting device and which moves together with the adjusting device during the adjusting process and by means of which the corresponding movement of the silhouette along the sensor surface is converted by the data processing unit into the amount of pharmaceutical to be delivered (e.g. insulin). The adjusting device is then the holder which movably fixes the component along a travel distance. The method relates in a further embodiment to determination of the position of a feed unit for removing a pharmaceutical from a cartridge. A feed unit converts the previously set amount of a pharmaceutical to be delivered into a movement of another component to deliver the pharmaceutical. The feed unit is connected firstly directly or indirectly to the stopper of the pharmaceutical cartridge and secondly directly or indirectly both to the presenting mechanism and the release mechanism to deliver the pharmaceutical. Determination of the position of the feed unit in the method according to the invention can take place through an element (e.g. geometrically shaped three-dimensional body or flat plate) which is fixedly connected to the feed unit, whereby a corresponding silhouette is generated on the sensor surface. In this case, the feed device is the holder which movably fixes the component along a travel distance.

To carry out the method there is use in a further embodiment of a data processing unit which is integrated in the medical apparatus, i.e. is a constituent of the medical apparatus. In a further embodiment of the method, the data processing unit is operated separately. It is possible to use for a such a separately operated data processing unit for example a PC on which a program suitable for operating the method of the invention is installed. Exchange of data and control signals between medical apparatus and data processing unit must then take place via suitable connecting pathways such as, in particular, cable connections, radio links or via data carriers.

In a further embodiment of the method, an aperture and/or a lens (for focussing or dispersion) is attached between the light source and the holder which movably fixes the component along a travel distance and/or the holder which movably fixes the component along a travel distance and the photosensitive sensor surface.

The light source consists in a preferred embodiment of the method of an LED row. The LED row may in this case give a diffuse beam. The individual LEDs of the LED row may have a small aperture angle. In a further embodiment, a converging lens, in particular a cylindrical lens, may be attached between the LED row and the component whose position is to be determined, or the holder which movably fixes the component along a travel distance.

In a further embodiment of the method, red light is generated by the light source. In another embodiment of the method, laser light is generated by at least two light sources aligned side by side. This laser light may in particular be red.

In another embodiment of the method, the sensor surface consists of a row of arranged sensor elements, such as, for example, a CCD line-scan camera. The arrangement takes place for example along a distance or in the form of a square or rectangular area. These sensor elements may have a wavelength-dependent sensitivity which is greatest in particular with red light.

The invention further relates to a device for carrying out a method according to the invention in one or more of the embodiments as described above, where this device comprises at least a) a light source (e.g. an LED row giving a normal or diffuse beam; or the individual LEDs with normal, large or small aperture angle; or the light source generating white, blue or red light; the light source generating laser light in white, blue or red color inter alia) and b) a holder which fixes, movably along a travel distance, a component (e.g. stopper of a pharmaceutical cartridge; or part of the metering device of a medical apparatus, in particular of an insulin pen; or part of the feed unit of a medical apparatus, in particular an insulin pen inter alia), and c) a photosensitive sensor surface (e.g. sensor elements arranged lengthwise in a row or on an area (e.g. CCD line-scan camera); or sensor elements with wavelength-dependent sensitivity; or sensitivity greatest with white, blue or red light) and d) a data processing unit (e.g. composed of an input unit for receiving data, central arithmetic unit, one or more memory elements, output unit for delivering the control signals, and connecting elements for the individual parts together with operating program, and program for evaluating the sensor surface in relation to occurrence of a silhouette and establishment of the position of the corresponding component, and evaluation relating to the time-dependent change in the silhouette along the sensor surface and establishing the position, and the moving the corresponding component).

The data processing unit may be an integral constituent of the medical apparatus or be operated separately from the medical apparatus. The integrated data processing unit comprises in this connection an operating system and a program for carrying out the position determination according to the invention. If the data processing unit is operated separately from the medical apparatus, exchange of data and control signals between medical apparatus and data processing unit takes place via suitable connections such as, in particular, cable connections, radio links or by movement of data carriers. A particularly suitable separately operated data processing system is a PC with operating system installed thereon and with a program for carrying out the position determination according to the invention.

A device according to the invention in one or more of the embodiments as described above can be used to assemble a medical apparatus which is suitable for administering a pharmaceutical (e.g. insulin, heparin, growth hormone, interferon, vaccine, antibody inter alia) into the human or animal body avoiding the gastrointestinal tract.

The invention additionally relates to a medical apparatus for injecting a pharmaceutical (e.g. an insulin) into the human body, the medical apparatus comprising inter alia a) a base element for mounting at least one technical component;
b) a technical component in the form of a receptacle for a pharmaceutical (e.g. cartridge), where the receptacle on the one hand an upper orifice which is closed fluid-tight by a stopper which is functionally connected to a plunger stem, and on the other hand a lower orifice which is connected to a cannula and through which a substance can be forced out of the reservoir by means of moving the stopper by the plunger stem;
c) a technical component in the form of a feed mechanism comprising on the one hand a plunger stem which is connected directly or indirectly to the stopper, and on the other hand a feed unit which, after actuation of a release, transfers the amount, which has been preset by means of a metering device (e.g. by fixing an angle of rotation), of the amount to be metered of the pharmaceutical in an appropriate movement of the plunger stem and of stopper;
d) a technical component in the form of a metering device for presetting the amount to be metered of the pharmaceutical,
e) a technical component in the form of a display (mechanical or LCD display) to display the amount, which has been preset by the metering unit and is to be administered by the medical apparatus, of the substance to be injected;
f) a technical component in the form of a release mechanism for starting up and carrying out the injection comprising in this case also the removal of air bubbles from the cartridge before carrying out the injection, which additionally comprises a device according to the invention in one or more of the embodiments as described above.

A medical apparatus of this type is in one embodiment in particular in the form and function of an insulin pen or of a pen suitable for injection of another pharmaceutical (e.g. heparin, growth hormone, interferon, vaccine, antibody inter alia).

In a further embodiment, a medical apparatus of this type includes at least one means for storing and/or processing data and/or signals, and at least one interface for transmitting data and/or signals to and/or from an external technical unit which is configured for the storage and/or processing of data and/or signals.

Such means and interfaces may be provided inter alia especially in the cap of the medical apparatus.

Said external technical unit may consist of a PC on which a program for storing and/or processing data and/or signals is installed.

A medical apparatus in one or more of the described embodiments can be used to inject insulin (normally acting, long-acting, short-acting) or GLP-1 or Lovenox or another substance.

The invention further relates to the production of a medical apparatus in one or more of the described embodiments for injecting a pharmaceutical into the human or animal body, where a) a base element is provided for mounting at least one technical component;
b) a receptacle (e.g. cartridge for a medicament, in particular insulin, heparin, GLP-1, peptide hormone, growth hormone, Lovenox, vaccine, antibody and the like) is provided;
c) a plunger stem is provided;
d) a feed mechanism is provided;
e) a metering device is provided;
f) a display is provided;
g) a release mechanism is provided;
h) possibly electronic constituents (e.g. means for storing and/or processing data and/or signals to and/or from a technical unit, e.g. a PC, which is configured for storing and/or processing data and/or signals) are provided;
i) a technical device according to the invention in one or more of the embodiments as described above is provided;
j) the individual constituents from a) to i) are assembled to give a functional unit.

The medical apparatus according to the invention can be used in particular for the prophylaxis and/or therapy of a disease and/or dysfunction of the body by means of a pharmaceutical whose pharmacological activity is diminished or lost in the gastrointestinal tract, such as, for example, the treatment of diabetes by insulin.

A device consists of one or more components and serves a particular medical purpose, in particular injection of a substance into the human or animal body. One component consists of one or more elements and serves to comply with a technical or non-technical function. A function is technical if it relates to a transfer of force, work, energy, material (substance), data and/or signals, the maintenance of the structure and/or form or the storage of a substance, or storage of information. A function is not technical if it relates to the input or output of information by or to the user of the device or of a substance by or to the user of the device.

A component may be for example part of the technical apparatus which provides a partial function in relation to the overall function of the apparatus.

A component is for example a reservoir. Reservoir may be an exchangeable cartridge comprising a substance (in particular a medicament such as, for example, insulin). The exchangeable cartridge may be suitable in particular for use in an insulin pen or another device for injecting a medicament into the human or animal body. Another example of a technical component is a device for pumping or a pump. Further examples of technical components are in particular syringes, needles, plunger stems, metering units, mechanical displays, tubing, seals, batteries, motors, transmissions, electronic displays, electronic memories or electronic controls. The meaning of purpose in connection with the technical device is intended to be in particular the movement of liquid from one place to another. One purpose is for example defined by moving a liquid volume from a reservoir to an outflow line. The purpose may also be injection of a medicament into the human or animal body.

A component may be connected in a technical manner to one or more other components in order to comply with a purpose together. A technical connection is for example a connection of components which is suitable for transmitting force, work, energy, material (substance), data and/or signals. The components can be connected for example via a mechanical coupling, a fixed mechanical connection (gluing, screwing, riveting, via linkage or the like), a toothed wheel, a latch, an interlock means, a metallic wire, an optical waveguide, a radio link, an electromagnetic field, a light beam or the like.

Injection is the introduction of substances in particular of liquids by means of a cannula together with syringe or functionally comparable device such as in particular a pen into the human or animal body. Inter alia, subcutaneous, intramuscular, intravenous, intracutaneous and intraarticular injection is known. Subcutaneous injection takes place underneath the skin and is relatively easy to carry out, not very painful and can be undertaken by the patient himself. Intramuscular injection takes place into a muscle. Since greater risks exist in this case, such as, for example, painful periosteal injury, this is usually undertaken by medical staff. Intravenous injection takes place following venepuncture directly through a vein.

In intracutaneous injection, a pharmaceutical is passed directly under the dermis. In intraarticular injection, a liquid is injected into a joint. Injection of a substance into the human or animal body is to be distinguished in particular from introduction of a substance through a medicament pump, an infusion or another type of continuous supply taking place over a certain time.

A cannula is essentially a hollow needle which is usually made of metal (e.g. steel, stainless steel, gold, silver, platinum). The end of the cannula is frequently sharpened by grinding at an angle. The cannula may be pointed and/or sharpened at one end and blunt at the other end, but it may also be pointed and/or sharpened at both ends. The cannula has at one of the two ends a usually conical attachment made of, for example, plastic by means of which the hollow needle can be arranged for example by pushing or screwing onto a medical apparatus such as, for example, a syringe, a medicament pen, in particular an insulin pen, a medicament container or a medicament pump. The cannula serves in functional interaction with a syringe, a pen, a pump or another medical apparatus suitable for this purpose, to remove or supply a liquid from or into the human or animal body.

The diameter of the cannula (external diameter) is usually stated in mm or in gage (18 gage=1.2 mm; 20 gage=0.9 mm; 21 gage=0.8 mm; 22 gage=0.7 mm; 23 gage=0.6 mm; 25 gage=0.5 mm; 27 gage=0.4 mm). Another parameter for characterizing the cannula is its length. Typical lengths of cannulas are 40 mm, 30 mm, 25 mm, 8 mm, 6 mm and other lengths.

A medical apparatus is in particular an apparatus for injecting the substance into the human or animal body. Besides the syringe, it is possible for such an apparatus for injection to be a medicament pen such as, for example, an insulin pen. Medicament pens are suitable in various form and for various purposes and are obtainable on the market from various manufacturers (e.g. Optiklick, Optipen, Optiset).

Every insulin pen must satisfy numerous requirements in relation to ease of operation in order to make safe and fault-free use possible. The basic requirement is for display of the preselected dose and of the amount remaining in the cartridge. The setting of the dose, and completion of the injection process should moreover be made audible, perceptible by touch and visible. This safety requirement arises in particular from the limited perception capacities of elderly type 2 diabetes patients.

Besides insulin pens with needles, also employed for insulin therapy are needle-free injection systems. A current example of the use of needle-free injection systems is the Injex injection system of Rösch AG. With this injector, extremely high pressure is used to shoot the insulin through a microneedle into the adipose layer of the skin. An elastic spring which is tensioned manually before injection stores the necessary injection energy therefor. The injected material is in this case distributed homogeneously and conically in the adipose tissue.

A non-negligible advantage of this apparatus is the needle-free injection of the medicament, which in some patients reduces the psychological inhibition threshold for insulin administration. In addition, needle-free injection precludes infection of the puncture site. Disadvantages when compared with conventional insulin pens proved to be the transfer of the insulin into special cartridges, the comparatively larger mass of the apparatus, and the inclusion of further accessories for tensioning the spring.

Insulin pumps differ from insulin syringes by being completely automatic infusion systems for continuous subcutaneous injection of insulin. They have approximately the size of a cigarette pack and are worn permanently on the body. Short-acting insulin is injected through a catheter and a needle located in the skin into the cutaneous tissue according to the program preset by the patient. The task of the insulin pump is to imitate the continuous output of insulin by the pancreas to reduce the blood glucose level, but without being able to regulate the blood glucose with closed-looped control. Because of the continuous and adaptable supply of insulin, these pumps have advantages in particular for people engaged in sporting activities and whose daily routine varies greatly. It is possible with insulin pump therapy to compensate for large variations in blood glucose, e.g. in diabetics with a pronounced DAWN phenomenon, which can be controlled with conventional methods only with increased effort. One disadvantage is that when the insulin supply is interrupted owing to the lack of an insulin reservoir in the human body, severe metabolic derangement may occur. Insulin pumps are available in various technical configurations, and apparatuses with syringe-like containers have become established during the technical development. In analogy to the insulin pens with needles, the insulin is present in a reservoir with movable stopper. The latter is moved by a motor-driven plunger stem.

Owing to the completely automatic and continuous delivery of insulin, the pumps are provided with a large number of security systems in order to protect the user from malfunctions with serious consequences. However, this does not mean that responsible and anticipatory use of the apparatus is unnecessary.

On the basis of the current injection apparatuses and further technological development in medical and microsystems technology there is an evident trend to completely automatic miniaturized medicament metering systems. Further development might go in the direction of implantable and extracorporeal medicament metering systems. The aim of implantable insulin pumps is to free the diabetic from the daily injection of insulin without the need to wear an external apparatus on the body.

Insulin pens are concentrate in the essential ergonomic and safety features in the EN ISO standard 11608. This likewise includes the geometric/material properties of the insulin cartridges and pen needles. The handling and the operation of a pen is thus substantially uniform and independent of the model for the user.

The contents of the EN ISO standard 11608 where this relates to insulin pens, insulin cartridges and needles is hereby expressly incorporated in the present disclosure by reference.

In the design of the pens there are some considerable differences to be found in the pens of the various manufacturers. The reasons therefor are for example the designation for different target groups (children, elderly people).

Because of the requirements of the EN ISO standard 11608, the differences are confined in particular to the injection mechanism and the release mechanism. The dose selector and the dose display are mostly subject to ergonomic requirements and result from the general design conditions of the respective model.

The essential functional element of an insulin pen is the injection mechanism. It determines the type and size of the pen and the design of the release mechanism and of the dose selector. The mechanism translates the dose preset on the dose selector with the injection energy derived from the release mechanism into an injection stroke of the stopper in the cartridge. This energy is transmitted either directly to the injection mechanism or through a motion-modifying transmission.

It is technically possible for the injection mechanism in the shape of the plunger stem to vary in form.

In the insulin pens currently available on the market, solutions with a rigid (e.g. threaded spindle, toothed rack) or a flexible (e.g. curved toothed rack, curved compression spring) design have become established. Other possible configurations such as telescopic plunger stem (e.g. screw mechanism, belt and chain drive, hydraulic transmission, coupled transmission) are not employed in the insulin pens currently commercially available.

The design solutions of the rigid and flexible type vary widely and depend on kind of pen, i.e. reusable pen or disposable pen. Plunger stems employed are threaded spindles or toothed racks or combinations of the two. In the dose selector, an angle of rotation corresponding to the dose is preset with the aid of detent devices and is transmitted by subsequent screw mechanisms and toothed gears to the injection mechanism and transformed into the injection stroke.

Delivery of the medicament takes place by specifying an injection stroke and the resulting displacement of the stopper. The amount of liquid delivered depends on the injection stroke and the internal diameter of the cartridge. To avoid dosage errors, air bubbles must be completely removed in accordance with manufacturers' specifications and the EN ISO standard 11608. In addition, after delivery of the liquid, a sufficiently long time should be allowed to elapse in order to ensure a steady state, i.e. normal pressure of the liquid and relaxation of the stopper in the cartridge.

The reservoir for the medicament (also referred to as cartridge) influences the construction and functional structure of the medicament pen. Partial functions which can be distinguished in this connection are firstly a protective function for the medicament, then a conveying function and finally a coupling function to the injection system of the medicament pen. The protective function is achieved by the cartridge as a whole, i.e. by stopper, glass body and sealing disk. The conveying function for the medicament is conferred by the stopper, which is displaced with the aid of the injection mechanism and brings about a change in volume in the cartridge. The coupling function to the injection system finally is produced by sealing means (e.g. sealing disk).

In an automatic medicament pen (e.g. automatic insulin pen), the injection energy is applied by drive with subsequent transmission. An energy supply and control unit are additionally necessary.

In the injection mechanism according to the invention, the medicament (e.g. through insulin) is conveyed not by displacement of the stopper by means of an injection mechanism, but by introducing a pump device. The pump device is inserted between cartridge and injection system and is to be provided with appropriate interfaces.

The pump device can be provided with a flow sensor. It is in direct contact with the medicament, e.g. insulin, thus giving rise to additional requirements such as reduced organism count, sterility, biscompatibility inter alia.

On application of this functional principle, numerous variables (e.g. the liquid pressure in the medicament container) are altered by comparison with a conventional medicament pen for injection (e.g. an insulin pen), because a sub-atmospheric pressure arises when the medicament is sucked out.

Insulin cartridges serve as primary packaging for the medicament and must satisfy high standards. This relates to the dimensional accuracy of the cartridge in relation to the accuracy of dosage and compatibility with other components. The ENO ISO standard 11608-3 is concerned with these requirements and describes the fundamental aspects and the geometrical/material construction without unnecessarily restricting the shape of the cartridge. The pharmaceutical impermeability of the cartridge must likewise be ensured.

The cartridges consist of a plurality of subcomponents. The principal one is the cylinder of pharmaceutical glass with high neutrality and chemical resistance to insulin. Before filling, the surface quality of the cylinder is improved by siliconization. This surface treatment reduces the sliding and breakaway forces of the stopper, increases the accuracy of dosage and reduces the dissolving out of glass constituents during a long storage time. The degree of siliconization correlates in this connection with the level of the frictional forces of the stopper, a limit being set by the sensitivity of the insulin to the silicone.

The cartridge is sealed at both ends by elastomeric closure parts, the stopper and the sealing disk. Crucial points in this connection are the demonstrated mechanical impermeability in various pressure situations, and the microbiological impermeability to all organisms in long-term tests. Further important points are the maximum allowable stopper forces and the number of punctures of the sealing disk with a cannula.

Pen needles are sterile disposable products employed to guide the insulin out of the cartridge into the target tissue. They are subject, just like cartridges, to strict requirements because the real functionality of the insulin pen is achieved only through cooperation of the two components. The needle consists of a cannula which is ground at both ends and which is set in a cartridge attachment piece. Optimized grinding of cannulas makes it possible for insertion into the target tissue to be substantially painless for the patient and causes only slight tissue damage on withdrawal again. Likewise, the cartridge sealing disk is pierced without extensive fragmentation. This is an obligatory requirement because the impermeability of the cartridge must be ensured also when the needle is regularly changed. The cartridge attachment piece ensures a firm fit on the insulin pen.

Even if pen needles show signs of wear which are scarcely visible to the eye after being used two or more times, they should nevertheless be changed after each injection for reasons of sterility. In addition, crystallized insulin may block the needle. Moreover, air gets into the cartridge if there are temperature variations, which equally causes dosage errors. Thus, a temperature change of only 15 K causes up to 15 µl of air to enter the cartridge.

Microfluidics is a subsection of microsystems technology and includes the design, production, use and investigation of microsystems which manipulate and treat amounts of fluid in channel cross sections with dimensions of from 1 µm to 1 mm.

Microfluidic systems are employed in medical technology, biochemistry, chemical engineering and analysis, and microreaction technology. These microsystems may have dimensions in the millimeter and centimeter range because it is the amount of fluid and not the size of the microfluidic system which is important for practical use. In addition, such systems show significant differences from conventional fluidic systems because of the small amounts of fluid and often small system sizes. Miniaturization is accompanied by a change in the behavior of the fluid flow because surface-linked effects and electrostatic and electrokinetic forces dominate. New approaches are therefore necessary for the design, production and characterization of microfluidic components, e.g. micropumps and sensors. The constant energy density of the actuators results in their output falling, so that they are not comparable with conventional components in the macro sector. For this reason, external actuators are frequently employed and at times considerably increase the dimensions of the overall system. In addition, the physics and chemistry of the particles and molecules to be transported limit the miniaturization of microfluidic components.

Diabetes mellitus is a disorder in which the body is itself unable to produce and appropriately use any, or sufficient, amounts of insulin. Insulin is required to transport glucose from the blood into the cells of the body. The blood glucose level is continuously kept constant within narrow limits (60-100 mg % or 3.33-5.55 mmol/l). This takes place through the interplay of the two hormones insulin and glucagon.

Diabetes mellitus is diagnosed after taking blood by means of appropriate laboratory apparatuses. An elevated blood glucose level must be detected on at least two different occasions in order to confirm the diagnosis.

Diabetes mellitus is the term used when the glucose level measured in the blood plasma exceeds the stated value in at least one of the indicated cases:
a) fasting blood glucose—7.0 mmol/l or 126 mg/dl
b) blood glucose two hours after a dose of 75 mg of glucose (oral glucose tolerance test)—11.1 mmol/l or 200 mg/dl
c) blood glucose 11.1 mmol/l or 200 mg/dl associated with severe thirst (polydipsia), frequent urination (polyuria) or loss of weight.

Untreated diabetes leads to elevated blood glucose levels which may lead to various symptoms and late consequences such as, for example, polyneuropathy, microangiopathy, macroangiopathy, retinopathy, nephropathy and others. The risk of late damage from diabetes is less when the nonenzymatic glycation of erythrocytes (HbA1c level) is lower.

Diabetic coma is a life-threatening acute complication of diabetes. The blood glucose level may in such cases extend above 1000 mg/dl, associated with excessive acidity in the blood (metabolic acidosis). Diabetic coma can be induced inter alia by infections, intake of too much carbohydrate, alcohol abuse or incorrect insulin dosage.

A distinction is made between type 1 diabetes and type 2 diabetes. In type 1 diabetes there is an absolute insulin deficiency from the outset and treatment is possible only with insulin dosage.

Type 2 diabetes is characterized by a reduced insulin sensitivity and a relative insulin deficiency. Type 2 diabetes can usually be treated initially with dietetic measures and tablets. Insulin replacement frequently becomes necessary during the course of the disorder.

Type 2 diabetes has become a widespread disease predominantly in industrialized countries. Overeating, lack of exercise and obesity are regarded as the main cause. Type 2 diabetes can be effectively counteracted by exercise training and diabetic measures, especially aiming at weight reduction. It is also possible in the case of type 2 diabetes to employ oral antidiabetics such as, for example, acarbose, biguanides, sulfonylurea, glitazone and others. Therapy using insulin is necessary when the blood glucose level can no longer be kept in or near the normal range with sufficient permanence by means of said measures.

Various insulins are available for insulin therapy. A distinction is usually made according to the duration of action or chemical structure. An analog insulin has different amino acids at individual positions compared with human insulin. The properties may be changed thereby.

The rapid-acting insulins include human insulin and various rapid- and short-acting insulin analogs such as glulisin (proprietary name: Apidra), lispro (proprietary name: Humalog) and aspart (proprietary name: Novo Rapid).

Slow-acting or extended-acting insulins are NPH insulin (human insulin with an action extended by neutral protamine hagedorn), zinc insulins and various insulin analogs such as glargine (proprietary name: Lantus) and detemir (proprietary name: Levemir).

Also used in insulin therapy are mixed insulins and recently inhaled insulins.

Mixed insulins consist of a rapid-acting insulin and an extended-acting insulin in various mixing ratios. 10/90%, 25/75%, 30/70%, 50/50% mixtures are usual. Insulin therapy must always be accompanied by regular determinations of the blood glucose level.

In conventional insulin therapy, a defined amount of mixed insulin is injected at fixed times. More intensive conventional insulin therapy is employed predominantly for the therapy of type 1 diabetics. In this case, a basic supply is ensured with an extended-action insulin (basal) and a rapid-acting insulin (bolus) is given additionally at meal times.

Continuous subcutaneous infusion of insulin by means of a pump is suitable namely for type 1 diabetics. The insulin is not injected but is passed into the body by a small pump. The pump is permanently present on the body. The insulin is supplied through a catheter with cannula. The insulin pump usually delivers rapid-acting insulin at small equal intervals over a prolonged period.

Glucagon-like peptide 1 (GLP1) is, alongside glucose-dependent insulinotropic peptide (GIP), one of the most important representatives of the incretins. Incretins are produced as hormones in the intestine and regulate inter alia the blood glucose level by stimulating insulin release in the pancreas.

The amount of intestinal hormones produced depends on the amount of carbohydrates taken in orally. The GLP1 level increases much more after oral glucose intake than after intravenous administration of glucose. It has been possible to show by investigations that intravenous infusion and subcutaneous injection of GLP1 in type 2 diabetics leads in many cases to complete normalization of the blood glucose level. A problem is that GLP1 is inhibited within a very short time by dipeptidylpeptidase IV (DPP-IV). Subcutaneous injection of GLP1 can maintain effective plasma concentrations over only about 1-2 hours. A solution in the direction of a persistent effect of GLP1 might be discoverable in the development of longer-acting GLP analogs or else inhibition of DPP-IV by pharmaceuticals.

Growth hormones are substances which stimulate growth in humans, animals and plants. Known examples are somatotropin (human), bovine somatotropin (cattle) and auxin, and gibberellic acid (plant).

Somatotropin (STH) is also known under the names human growth hormone (HGH) and growth hormone (GH). STH is a peptide hormone with 191 amino acids. Production takes place in the anterior pituitary under the control of somatotropin-releasing factor (SRF; GHRH; GRF) from the hypothalamus. STH is absolutely necessary for normal linear growth. Reduced production of or reduced response of the cells to STH results in short stature. Overproduction results in gigantism or acromegalie.

Short stature caused by growth hormone deficiency has been treated for some years by administration of STH. It was initially obtained from cadaver pituitaries before it became possible to produce STH by genetic manipulation in 1985.

Interferons are produced as tissue hormones by human or animal leucocytes, fibroblasts or T lymphocytes. An interferon is a protein or glycoprotein with an immunostimulating (e.g. antiviral) or antihormonal effect. Interferons are divided into alpha-interferons, beta-interferons and gamma-interferons. Interferons are obtainable from various manufacturers for indications such as viral diseases (e.g. SARS), cancer, multiple sclerosis, hepatitis B/C, hepatitis C.

A vaccine is a composition produced biologically or by genetic manipulation and comprising inter alia individual proteins and/or RNA or DNA fragments and/or killed or attenuated pathogens (e.g. influenza, SARS, poxvirus, pathogens of measles, mumps, rubella, poliomyelitis, pathogens of whooping cough).

Known types are live vaccines (e.g. cowpox), attenuated live vaccines with attenuated viruses or bacteria (e.g. MMR vaccine, yellow fever, poliomyelitis) and dead vaccines with inactivated or killed viruses or bacteria or constituents thereof (e.g. influenza, cholera, bubonic plague, hepatitis A).

Heparins are substances employed therapeutically to inhibit blood coagulation. Heparins consist of in each case alternating sequences of D-glucosamine and D-glucuronic acid or L-iduronic acid. Chain lengths consisting of 5 units may be sufficient for anticoagulation.

The polysaccharide chains mostly have a molecular weight of between 4000 and 40 000. Besides unfractionated heparins, use is also made of lower molecular weight fractionated heparins with a molecular weight of about 5000. Heparins are not absorbed from the gastrointestinal tract but must be administered parenterally. Heparins act by binding to antithrombin III and thus accelerating the inactivation of activated coagulation factors.

Lovenox (also known as clexane) is a commercially available pharmaceutical preparation with the pharmacologically active ingredient enoxaprin sodium. The active ingredient is one of the low molecular weight heparins with a linear dose-response relation and a constantly high bioavailability.

Areas of indication for Lovenox are the primary prophylaxis of deep vein thromboses, therapy of deep vein thromboses with or without pulmonary embolism, therapy of unstable angina pectoris and of the so-called non-Q-wave myocardial infarction, and thrombosis prophylaxis and anticoagulation during hemodialysis.

EXAMPLE

Construction of a measuring apparatus for transillumination of a cartridge, receiving the silhouette, transferring the measurements to a PC and subsequent image analysis.

The measuring assembly consists of a light source, slits, a cartridge with fixing device and a line-scan sensor.

The light source comprises in each case alternatively an LED row giving a diffuse beam, an LED row composed of LEDs with small aperture angle or point source with converging lens. The line-scan sensor used is a CCD line-scan camera without lens with wavelength-dependent sensitivity (maximum in the red spectral range).

To reduce the stray radiation, slits are present in front of and behind the cartridge.

The cartridge is transilluminated in a plane in the middle position. The silhouette consists of partial shadows and complete shadows of the stopper. After the intensity measurements of the individual sensor elements have been digitized and transferred to the PC, the stopper position is ascertained by an appropriate software by determining the pixels which are below a certain brightness (threshold comparison).

The recognition system is suitable in particular in injection pens for measures for metering and determining the amount administered.

The measuring apparatus consists of the three main components of light source, line-scan sensor with slit and evaluation electronics (FIG. 1). Light-emitting diodes with an aperture angle of about 6°, arranged in a row, are used as light source. Thus, with a suitable arrangement it is possible to achieve a uniform illumination of the cartridge which is necessary for edge identification. A slit is present between the light source and the cartridge to improve the contrast and accuracy of measurement. It is necessary in order to compensate for fluctuations in brightness at the sensor due to differences in refraction of the light when the cartridge is full and empty, and in order to avoid stray light through total reflection on the glass cylinder.

The line-scan sensor has a total of 1280 pixels with a pixel distance of 63.5 µm and completely detects the silhouette of the cartridge. The photosensitive pixels of the sensor convert the incident light into electrical signals whose values depend on the intensity of light and the integration time. The sensor electronics transfers sensor values with a gradation of 8 bit to an interface to the evaluation electronics. Dark areas, e.g. in the complete shadow behind the stopper, have a value near zero in this case. When operated with ambient light, the sensor is overloaded after about 2 ms, and the evaluation of the silhouette is no longer possible. The sensor system is therefore in the case of the laboratory model shielded by being present in the lightproof housing. The sensor data are evaluated by a measurement computer and the LabView software. An adapted program processes the sensor data and calculates the stopper position with an edge identification algorithm. The clock interval for calculating the stopper position is about 20 ms, as a result of the computing power of the measurement computer, the data transmission between sensor and PC, and the intensity of the silhouette. The metering process and the conveying device are controlled in terms of software by converting the stopper position into a volumetric quantity. A characteristic silhouette with the typical optical effects correlating with the stopper position is shown in FIG. 1. The previously described different distribution of brightness between filled and empty glass cylinder is evident. In addition, the disturbances at the top and end of the cartridge, owing to the cartridge geometry, are easily recognizable. This makes a differentiation necessary in the edge identification and the division of the cartridge into a plurality of regions. The greatest accuracy of measurement is in this connection achieved in the middle region of the cartridge because a homogeneous glass structure is present there.

FIG. 1: Characteristic Intensity Distribution on the Glass Cartridge with Parallel Incident Light Reflections occur at the shoulder and end of the cartridge due to curvature and inhomogeneity of the glass and impede threshold identification. The stopper position is identified in three steps, of compensation for clock interval deviations, of edge identification and of calculation of the stopper position with correction of optical effects. In the first step, errors in the intensity value owing to clock interval deviations are compensated by the computer. In normal operation, owing to the use of a measurement computer, deviations in the clock interval and in the integration time of up to 2 ms occur. The result thereof is, even with the same illumination, different brightness values on the respective pixel, and these can be compensated by measuring the actual integration time. A further possibility is to reduce the effect of pixel noise by averaging. In the second step, the edges are determined by threshold identification. The brightness distribution in FIG. 1 shows a clear separation between the shaded region of the stopper and the bright, directly illuminated region. In this case, the first edge results from the position of the pixel whose brightness is the first to be below a previously fixed threshold. The second position is determined by the pixel position with a brightness value which is above the threshold. If the threshold is between two pixels, the position is determined by interpolation, simultaneously improving the resolution of the edge position. In the third step, the stopper position is calculated on the basis of the stopper edges. It is necessary for this to differentiate depending on the stopper position:

1) In region 1 at the start position, the stopper position is calculated on the basis of the position of the front edge. The maximum measurement error corresponds to the single pixel distance of 64 µm.
2) In cartridge region 2, the stopper position is afforded by the position of the front edge and rear edge. The maximum measurement error in this region is about 32 µm, corresponding to half the width of a pixel.
3) In cartridge region 3, the position of the rear edge of the stopper is used. This results in a measurement error of a single pixel width of about 64 µm. For error-free transmission of the stopper position it is likewise possible to use the width of the stopper.

When switching between the individual regions, the measured width of the stopper is used to assist in avoiding jumping over the stopper position.

DESCRIPTION OF THE FIGURES

FIG. 1: Sensor system to identify the stopper position (without evaluation electronics)

Figure 2:
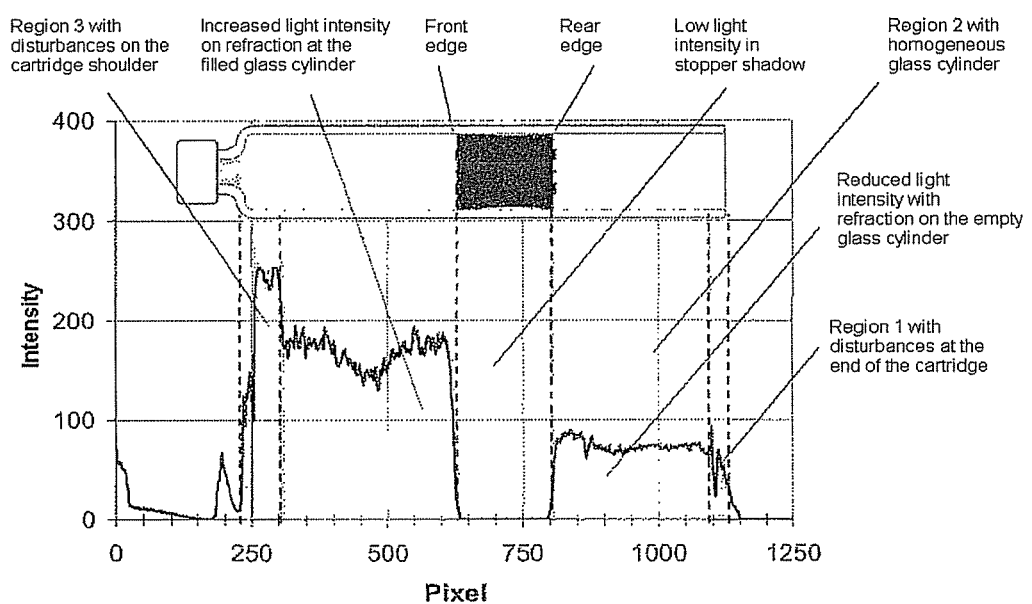
FIG. 2 shows a characteristic intensity distribution on the glass cartridge with parallel incidence of light.

FIG. 2: Characteristic intensity distribution on the glass cartridge with parallel incidence of light

What is claimed is:

1. A method for determining the position of a component of a medical apparatus along a travel distance by means of
   a) a light source comprising an LED row,
   b) a holder that fixes the component movably along a travel distance,
   c) a photosensitive surface of a sensor, and
   d) a data processing unit,
   wherein the method comprises:
      initially generating a silhouette of the component on the photosensitive surface by irradiating the component with light from the light source to create a first region of the photosensitive surface irradiated with light having a first intensity and a second region of the photosensitive surface irradiated with light having a second intensity, wherein the second intensity is greater than the first intensity, wherein the medical apparatus is configured such that light resulting from irradiating the component that reaches the photosensitive surface of the sensor did not pass through a lens between the holder and the photosensitive surface, and wherein the component is a solid component;
      determining a boundary between the first region of the photosensitive surface and the second region of the photosensitive surface;
      determining a location of the boundary on the photosensitive surface; and
      converting, using the data processing unit, the location of the boundary on the photosensitive surface into the position of the component of the medical apparatus along the travel distance.

2. The method as claimed in claim 1, wherein the component of the medical apparatus whose position is determined is a stopper of a cartridge for a pharmaceutical, or a component connected to a stopper of a cartridge for a pharmaceutical.

3. The method as claimed in claim 2, wherein the pharmaceutical is insulin.

4. The method as claimed in claim 2, wherein the light source transilluminates the cartridge.

5. The method as claimed in claim 4, wherein the data processing unit determines whether a portion of the cartridge is full or empty based on the second intensity of light on the second region of the photosensitive surface.

6. The method as claimed in claim 1, wherein the component whose position is to be determined relates to an adjusting device used to preset an amount of a pharmaceutical to be delivered.

7. The method as claimed in claim 1, wherein the component whose position is determined relates to a feed unit for removing a pharmaceutical from a cartridge.

8. The method as claimed in claim 1, wherein the data processing unit is integrated in the medical apparatus.

9. The method as claimed in claim 1, wherein a separate data processing unit is operated together with the medical apparatus.

10. The method as claimed in claim 1, wherein an aperture is disposed between the light source and the holder, and a second aperture between the holder and the photosensitive surface.

11. The method as claimed in claim 1, wherein an aperture is disposed between the light source and the holder, or is disposed between the holder and the photosensitive surface.

12. The method as claimed in claim 1, wherein the LED row gives a diffuse beam.

13. The method as claimed in claim 1, wherein each individual LED of the LED row has a small aperture angle.

14. The method as claimed in claim 1, wherein a converging lens is disposed between the LED row and the component.

15. The method as claimed in claim 14, wherein the converging lens is a cylindrical lens.

16. The method as claimed in claim 1, wherein the light source generates red light.

17. The method as claimed in claim 1, wherein the photosensitive surface comprises a row of arranged sensor elements.

18. The method as claimed in claim 17, wherein the sensitivity of the row of arranged sensor elements is greatest with red light.

19. The method as claimed in claim 1, wherein the sensor is a line-scan sensor.

20. The method as claimed in claim 1, wherein the first intensity is zero or substantially zero.

21. The method as claimed in claim 1, wherein a slit is disposed between the light source and the component.

22. The method as claimed in claim 1, wherein the holder comprises a sidewall of a cartridge in which the component is disposed.

* * * * *